United States Patent [19]

Wagner et al.

[11] Patent Number: 5,175,385

[45] Date of Patent: Dec. 29, 1992

[54] VIRUS-RESISTANT TRANSGENIC MICE

[75] Inventors: Thomas E. Wagner; Xiao-Zhuo Chen, both of Athens, Ohio

[73] Assignee: Ohio University/Edison Animal Biotechnolgy Center, Athens, Ohio

[21] Appl. No.: 92,514

[22] Filed: Sep. 3, 1987

[51] Int. Cl.$^5$ ............................................. C12N 15/00
[52] U.S. Cl. .................................. 800/2; 800/DIG. 1; 435/172.3; 435/320.1; 435/317.1; 935/111
[58] Field of Search ...................... 435/68, 172.3, 320, 435/240.2, 811, 320.1, 317.1; 800/1, 2, DIG. 1; 935/11, 32, 36, 63, 64, 70, 53

[56] References Cited

U.S. PATENT DOCUMENTS

| | | | |
|---|---|---|---|
| 4,262,090 | 4/1981 | Colby et al. | 935/108 |
| 4,276,282 | 6/1981 | Sugimoto et al. | 435/68 |
| 4,497,796 | 2/1985 | Salser et al. | 935/62 |

OTHER PUBLICATIONS

Palmiter, et al.; Science 222:809-814 (1983); Metallothionein-Human GH Fusion Genes Stimulate Growth of Mice.

Zinn, et al.; PNAS 79:4897-4901 (1982); Regulated Expression of an Extrachromosomal Human beta-Interferon Gene in Mouse Cells.

Weissman, et al.; Progress in Nucleic Acid Research and Molecular Biology, vol. 33, pp. 251-301; The Interferon Genes.

Hammer, et al.; Nature, vol. 315, pp. 680-683; Production of Transgenic Rabbits, Sheep and Pigs by Microinjection.

Pursel, et al.; Vet. Immunol. and Immuno. 17, (1987) 303-312; Progress on Gene Transfer in Farm Animals.

Simons, et al.; Bio/Technology, vol. 6 (Feb. 1988) 180-83; Gene Transfer into Sheep.

Salter, et al.; Virology 157;236-40 (1987); Transgenic Chickens:Insertion of Retroviral Genes into the Chicken Germ line.

Zuoyan, et al.; Kexue Tongbao, vol. 31, No. 14, (Jul. 1986) 988-90; Biological Effects of Human Growth Hormone Gene Microinjected into the Fertilized Eggs of Loach.

MacLean, et al.; Bio/Technology, 5:257-261 (1987); Introduction of Novel Genes into Fish.

Rusconi, et al.; Proc. Natl. Acad. Sci. vol. 78; No. 8; 5051-55 (Aug. 1981); Transformation of Frog Embryos with a Rabbit $\beta$-Globin Gene.

McCullagh, et al.; Journal of Interferon Research; vol. 3, No. 1 (1983) 97-111; Biological Properties of Human Interfereon Beta 1 Synthesized in Recombinant Bacteria.

Wilkinson, et al.; Methods in Enzymology, vol. 119, pp. 96-103; Preparation and Partial Purification of Human Interferon $\epsilon$.

Weck, et al.; J. Gen Virol (1981), 57:233-237; Comparison of the Antiviral Activities of Various Cloned Human Interferon-$\alpha$ Subtypes in Mammalian Cell Cultures.

Weck, et al.; Infection and Immunity (Feb. 1982) 660-65; Antiviral Activity of Bacteria-Derived Human Alpha Interferons Against Encephalomyocarditis Virus Infection of Mice.

Streuli, et al.; Proc. Natl. Acad. Sci. vol. 78, No. 5, 2848-52 (May 1981); Target Cell Specificity of Two Species of Human Interferon-$\alpha$ Produced in Escherichia coli and of Hybrid Molecules Derived from them.

Weck, et al.; J. Gen. Virol (1983), 64:415-19; Antiviral Effects of Human Fibroblast Interferon from Escherichia coli against Encephalomyocarditis Virus Infection of Squirrel Monkeys.

(List continued on next page.)

*Primary Examiner*—Elizabeth C. Weimar
*Assistant Examiner*—Jasemine C. Chambers
*Attorney, Agent, or Firm*—Iver P. Cooper

[57] ABSTRACT

A transgenic mouse with enhanced viral resistance transmissible to its offspring is prepared by introduction of a gene encoding a human interferon having antiviral activity into a host mouse. The gene encodes the interferon of a different animal species and therefore its expression product is less toxic to the host at an embryonic, fetal, neonatal or junvenile stage of development. Preferably, the human beta interferon gene is introduced into the cells of a mouse.

8 Claims, 4 Drawing Sheets

OTHER PUBLICATIONS

"The Structure of One of the Eight or More Distinct Chromosomal Genes for Human Interferon-Alpha", Nagata, et al., Nature, 287:4 1-408 (1980).

"Transgenic Mice Carrying Exogenous Mouse Interferon Genes", Kawade et al., Biol. Interferon Syst., Proc. ISIR-TNO Meet. Interferon Syst. 1986 (Pub. 1987) pp. 305-311.

"The Human Beta-Globin Gene and a Functional Viral Thymidine Kinase Gene in Developing Mice", Wagner et al., PNAS, 78:5016, 1981.

"Studies of Foreign Genes Transmitted Through the Germ Lines of Transgenic Mice", Jon W. Gordon, J. Exper. Zool., 228: 313-324, 1983.

Palmiter et al., Science 222: 809-814 (1983).

Zinn et al., Proc. Natl. Acad. Sci. 79: 4897-4901 (1982).

Van Brunt, BioTechnology 6 (10): 1149-1154.

Wilmut et al., New Scientist, Jul. 7, 1988, pp. 56-59.

Gordon, J. Exp. ZOOC 228 (2) pp. 313-324 (1983) C.A. 100: 115805s.

Gordon et al., Science 214 pp. 1244-1246 (1981).

Kawade et al., Biol. Interferon Syst. Proc. ISIR-TNO 1986 pp. 305-311, C.A. 107:128406.

Wagner et al., Proc. Natl. Acad. Sci. 78(10) pp. 6376-6380 (1981).

Gresser et al., Nature 258 pp. 76-78 (1975).

VIRUS-RESISTANT TRANSGENIC MICE

BACKGROUND OF THE INVENTION

1. Field of the Invention

This invention relates to the production of virus-resistant transgenic animals.

2. Information Disclosure Statement

Viral infections in agricultural animals represent a major economic loss for farmers and ranchers. Significant viral diseases in cattle are infectious bovine rhinotracheitis, parainfluenza, bovine viral diarrhea, rabies, and foot and mouth disease. In swine, transmissible gastroenteritis, swine mycoplasmal pneumonia, pseudorabies, and rabies infections are serious health problems. Poultry production is hampered by Marek's disease, Newcastle disease, infectious bursal disease, and infectious bronchitis, all of which are viral diseases. In 1981, over $500,000,000 was spent to treat agricultural animals against viral infections and the economic loss to agriculture resulting from viral disease is substantially greater that this cost.

One method of providing virus resistance is by use of vaccines. Vaccination may be with attenuated or inactivated virus, or with viral proteins produced by genetic engineering techniques. Vaccination, unfortunately, has many disadvantages. The animals must receive separate immunizations for each disease-causing organism. Moreover, the immunity diminishes with time and must be restored by follow-up immunizations, a practice which is inconvenient in the case of livestock allowed to roam on free range.

Another approach is that of treatment with an antiviral drug. Such drugs include acyclovir, ribovirin, adenine arabinoside and amantadine. A drug of particular interest is interferon, or, more especially, the various species of alpha (leukocyte) and beta (fibroblast) interferon. Collectively, these are called Type I interferons. The antiviral activity of various mammalian interferons is reviewed in Colowick, S. P. and Kaplan, N. O. Interferons, S. Pestka (Ed.), *Methods in Enzymology*. Orlando: Academic Press, Inc., 1986, Vol. 119(C). The interferons do not act directly against the virus, rather, they stimulate the antiviral response of the immune system. The antiviral activities of exogenous interferons in animals are reviewed by Stewart II, THE INTERFERON SYSTEM, 282-283, Table 16 (2d ed. 1979). Unfortunately, the antiviral drugs are expensive and provide protection for only a short period of time.

Kawade, et al., at the 1986 ISIR-TNO Annual Meeting, September 7-12, 1986, reported the production of transgenic mice carrying mouse interferon beta or gamma genes coupled to the mouse MT-I or heat shock promoters. According to Kawade, linearized plasmid DNA was microinjected into fertilized mouse eggs. Twenty-eight pups were born, four of whom carried the chimeric IFN genes. Three of these transmitted the genes to offspring. Apparently, Kawade had not determined whether the chimeric gene was actually expressed in the mice, but had already been able to express it in cultured cells induced by $Cd^{2+}$ or by heat. Our invention relates to the introduction of the interferon gene of another animal species into a host animal, and to the production of a healthy transgenic animal with enhanced viral resistance which it can genetically transmit to its offspring.

Gordon and Ruddle, Science, 214:1244 (1981) claimed integration and stable germline transmission of genes injected into mouse pronuclei. Ten thousand copies of a human leukocyte IFN gene were microinjected into each zygote. Ten mice were born from 33 implanted embryos; one of the mice was transgenic. Expression was not reported, and the purpose of the study was to show that the technique could be used to study gene action during mammalian development.

Staehelin, WO 87/00864 (publ. February 12, 1987) observed inhibition of influenza virus in NIH 3T3 mouse cells genetically modified to express the mouse protein Mx. This protein is one whose production is stimulated by mouse interferon. Staehelin suggested that an animal could be protected against viral infection by inserting a gene encoding the Mx protein into that animal, preferably at the single cell embryo stage. He taught that the gene of choice would be the one encoding the Mx protein that is normally found in the species of animal to be protected. He did not suggest use of the interferon gene, or of a gene derived from a different species than the host.

The expression of an exogenous gene in a transgenic animal is a far more subtle process than the expression of the same gene in mammalian cell culture. Expression of the gene at the wrong time may kill the animal. The problem is particularly acute when the gene is inserted into an embryonic cell, since the developing embryo, fetus or neonate may be distinctly sensitive to the gene product. It is known that mouse interferon is toxic to newborn mice. Gresser, et al., Nature, 258:76-78 (1975).

There is considerable controversy as to the cross-species antiviral activity of interferon.

Wilkinson and Morris, Methods Enzymol., 119:96 (1986) reported that human IFN-beta had little antiviral activity on bovine EBTr (0.2) and murine L-929 (0.03) cells (activity on human GM 2767 cells taken as 100). McCullagh, et al., J. Interf. Res., 3:97 (1983) credits human beta-IFN with somewhat greater activity on mouse cells, but still much less than on human cells.

With respect to IFN-alpha, species, A, B, C, D and F all showed low antiviral (VSV) activities (0.5-5) on mouse L-929 cells relative to WISH cells (100), according to Weck, J. Gen. Virol., 57:233 (1981). Streuli, et al., PNAS, 78:2848 (1981) credited alpha-1 interferon with a somewhat higher activity on L929 cell (10% of activity on bovine cells, activity in WISH cells was 20% of bovine cell activity). However, certain alpha-1/alpha-2 hybrid interferons had higher activities on mouse cells (100-170% of bovine cell activity). See also Weck, et al., Infection & Immun., 35:660 (1982), Weck, et al., J. Gen. Virol., 64:415-419 (1983).

Bell, EP Appl 163,993 (publ. Dec. 11, 1985), Bell, EP Appl 131,818 (publ. Jan. 23, 1985), and Bell, EP Appl 130,564-566 (publ. Jan 9, 1985), describe the preparation of a beta-IFN analogue by rDNA techniques and suggests that it may be useful in treating viral infection ('993, claim 36). No reference is made to the creation of transgenic animals.

Itoh, EP Appl 83,069 and Crea, EP Appl 48,970 disclose bacterial expression of a human beta-IFN gene under the control of a trp promoter. Guarente, EP Appl 42,246 also relates to bacterial expression of beta-IFN, but as part of a hybrid protein.

Mark, U.S. Pat. No. 4,588,585 relates to an IFN-beta analogue. It is suggested that this protein may be useful in diagnosis and treatment of viral and other infections. (col. 20)

Eppstein, U.S. Pat. No. 4,606,917 discloses a synergistic composition of DHPG and beta-IFN for use in treating antiviral infections.

Thompson, EP Appl 217,645 describes a stabilized IFN-beta or IL-2 composition for antiviral use.

TORAY, JP 61052285 (abstract) discloses expression of IFN-beta in a eukaryotic cell, under control of, for example, the MT promoter.

Gruneberg, EP Appl 34,306 (abstract) describes expression of IFN-beta in a microorganism.

Sugano, WO 82/02715 (abstract) describes expression of IFN-beta in a eukaryotic cell.

Palmiter, WO83/01783 teaches that a structural gene may be coupled to the MT promoter, introduced into the embryo of a mouse, and expressed in the adult mouse after induction with heavy metals. Palmiter worked with both thymidine kinase and rat growth hormone. Palmiter suggested that the MT promoter could be used to control transcription of other genes in higher animals, including genes relating in some manner to "disease resistance". (page 31).

Hamer, WO84/02534 discloses expression of HGH in mammalian cell culture under control of the MT promoter.

Karin, U.S. Pat. No. 4,601,978 generally suggests inducible expression of heterologous genes in mammalian cells under the control of the human MT II gene.

Kushner, WO86/04920 relates to expression of HGH and certain other proteins (IFN is not mentioned) under the control of the human MT II promoter in CHO cells.

The foregoing information is disclosed because it might be considered material by the Examiner in the course of examining this application. No admission is made that any of this information constitutes prior art or pertinent prior art, that the references themselves accurately or completely describe the work reported, or that the dates of publication given are exact.

SUMMARY OF THE INVENTION

This invention rests in the production of transgenic animals with inherent viral resistance which will persist throughout their lives and, in a preferred embodiment, be transmitted to their offspring. This viral resistance will be conferred by the gene encoding an alpha or beta interferon, preferably the latter, of an animal species other than that to which the host animal belongs. Preferably, the human interferon gene is introduced into the genome of animals other than man.

The native interferon gene is expressed, if at all, only at very low levels, prior to its induction by virus. However, it is desirable to provide for interferon expression prior to the onset of viral infection. In one embodiment of this invention, a promoter is used which is at least partly constitutive, so that significant amounts of interferon are expressed by the animal at all times.

It may be undesirable, however, to use an interferon gene which is native to the animal species to which the host animal belongs (a "homologous" gene). The expression production of that gene is likely to be more active in the host than that of a heterologous gene, and therefore more likely to have an adverse effect. Since human beta interferon is less active in mice, for example, than in our own species, its continuous delivery is less likely to have a toxic effect. Since the human interferon is expressed intracellularly, the presence or absence of cell surface receptors for human interferons is irrelevant.

In another embodiment, the promoter is a wholly or partly inducible promoter which is induced prior to the onset of viral infection, and, preferably, when the risk of infection is increased. For example, expression might be induced prior to shipping, or when a neighbor's herd is infected.

The claims appended hereto are incorporated by reference as descriptions of the preferred embodiments.

BRIEF DESCRIPTION OF THE DRAWINGS

FIG. 3 shows an antibody-antigen neutralization CPE assay. Rows and A and B contain serum from transgenic mice. Row B additionally contains anti-human IFN beta antibody. Rows C-F all contain serum from normal mice. C also contains IFN standard; D, IFN standard plus antibody, and F, antibody. Row G contains IFN standard only. Row H contains cell (M1 to M6) or virus (H-7 to H-12) controls. The columns represent successive two-fold dilutions of the above from the contents of the first column. All samples were incubated overnight with human WISH cells, challenged with VSV for 48 hours, and stained with crystal violet. It will be noted that the serum from the transgenic mice apparently contains human beta interferon, as it protects human cells from viral infection and is neutralized by an anti-human beta interferon antibody.

DETAILED DESCRIPTION OF THE INVENTION

The term "animal" is used herein to include all vertebrate animals, except humans. It also includes an individual animal in all stages of development, including embryonic and fetal stages. A transgenic "animal" is any animal containing one or more cells bearing genetic information received, directly or indirectly, by deliberate genetic manipulation at a subcellular level, such as by microinjection or infection with recombinant virus. The term is not intended to encompass classical crossbreeding or in vitro fertilization, but rather is meant to encompass animals in which one or more cells receive a recombinant DNA molecule. This molecule may be integrated within a chromosome, or it may be extrachromosomally replicating DNA. The term "germ cell line transgenic animal" refers to a transgenic animal in which the genetic information was introduced into a germ line cell, thereby conferring the ability to transfer the information to offspring. If such offspring in fact possess some or all of that information then they, too, are transgenic animals.

The information may be foreign to the species of animal to which the recipient belongs, foreign only to the particular individual recipient, or genetic information already possessed by the recipient. In the last case, the introduced gene may be differently expressed than the native gene.

The transgenic animals of this invention may be of any vertebrate species, other than man, which is responsive to interferon. Farm (e.g., horse, cow, pig, goat, sheep) and pet (e.g., dog, cat) animals ar of particular interest. Interferons have been demonstrated in fish, reptiles, birds, and mammals, including primates, felines, bovines, canines, and rodents. The interferon gene may likewise be derived from any vertebrate species other than the species of the intended host animal. The human, bovine and murine interferon genes are the best characterized. See Weissmann and Weber, Progr. Nucl. Acids Res. & Mol. Biol., 33:251–300 (1986). The use of human interferon gene is preferred.

The interferon gene may be any interferon gene species which cells express in response to viral infection. These presently fall into two major classes, alpha and beta interferon, which in turn may be divided into various subclasses. However, this invention would encompass use of other classes of interferon having antiviral activity. Besides using the naturally occurring gene, one may use genes which have been modified for altered expression in the intended host or for production of a modified protein having enhanced antiviral activity.

The introduced interferon gene generally should not encode the same interferon as the interferon native to the host animal, and its expression product preferably should be more homologous to the interferon of a different animal species than to that of the host animal. However, it is conceivable that a more modestly modified interferon will fall within the compass of the present invention if, it is of reduced toxicity. It is also conceivable that a minor interferon species, native to the host, will have sufficiently low activity to be useful in the present invention.

The genes may be obtained by isolating them from genomic sources, by preparation of cDNAs from isolated mRNA templates, by direct synthesis, or by some combination thereof. The published sequences of numerous alpha and beta IFN genes greatly facilitates obtaining a gene encoding an antiviral IFN, and this invention is not limited to the use of any particular gene. However, the human beta-1 interferon gene is preferred. It is important that the added gene have sufficient activity to enhance viral resistance but not enough to induce other, toxic responses.

To be expressed, the structural gene must be coupled to a promoter in a functional manner. If a constitutive promoter is used, a viral promoter, such as the SV40 early promoter, is preferred. The MT promoter, while often referred to as an "inducible" promoter, is best described as "semi-constitutive," since it is "on" all of the time, even though its activity is boosted by heavy metal ions. Such promoters, as well as pure inducible promoters, may also be used. Promoter/regulatory sequences may be used to increase, decrease, regulate or designate to certain tissues or to certain stages of development the expression of interferon. The promoter need not be a naturally occurring promoter.

In mammals, the exogenous interferon gene may be introduced by zygote microinjection as described below for the mouse. In avian species, the interferon gene may be introduced through the use of avian retroviral vectors. The interferon gene may also be introduced into non-germline cells (somatic cells) in a fetal, new born, juvenile or adult animal by retroviral vector mediated genetic transformation of somatic cells of one or more tissues within the animal.

EXAMPLE 1

Construction of MT-IFN Plasmid

The MT-IFN plasmid was derived from plasmid pMK, see Palmiter, et al., Cell, 29:701–10(1982) which contains methallothionein I (MT-I) promoter; and plasmid pIFR, see Zinn, et al., Cell, 34:865–79(1983) which contains a genomic human beta interferon gene and its 3' flanking sequence. An EcoRI/Bgl II 1.8 kb MT-I promoter was fused to the h-IFN-beta structural gene by the following procedure: pMK was linearized by Bgl II and pIFR was linearized, by Nco I; then both plasmids were blunt ended by a Klenow "filling-in" reaction. Both blunt ended plasmids were subsequently cut by EcoRI which left both plasmids with two compatible ends: EcoRI and blunt. Then 1.8 kb MT-I promoter was inserted into pIFR by a sticky/blunt ligation. This plasmid was named pMTIF-beta A. Because of the DNA sequence generated at the junction of the MT-I promoter sequence and the interferon structural gene, an ATG codon was introduced into the resulting fusion gene. The nucleotide sequence ATG codes for the initiation of transcription of the DNA sequence into RNA, but initiation from this "spurious" ATG results in an RNA message in an improper reading frame which is transcribed into a protein other than interferon. The appropriate ATG sequence in the correct reading frame to express authentic human interferon is also present within this fusion gene. Competition between the two ATG initiation sites results in a decrease in the amount of authentic human interferon message. Therefore, the additional ATG is eliminated by the following method: pMTIF-beta was first linearized by NcoI cleavage, followed by a nuclease S1 "chewing back" reaction (because additional ATG codon is right on the 5' overhang, single strand nuclease activity of nuclease S1 will blunt end the Nco 1 site so that the additional ATG will be deleted). Finally, the plasmid was recircularized by blunt-end ligation. This plasmid was named pMT1F-beta B also known as pMTIF-Beta$_1$ B.

Plasmit pMTIFN-beta$_1$ B was deposited under the Budapest Treaty with the american Type Culture Collection, 12301 Parklawn Drive, Rockville, Maryland 20852 on Dec. 13, 1991, and assigned the accession number ATCC 75172. After issuance of a patent on this application, the ATCC will make the plasmid available to requesters in accordance with the Budapest Treaty and U.S. patent laws and regulations. This deposit is not a license to practice the invention, and no admission is made that deposit was necessary to satisfy U.S. law.

EXAMPLE 2

Figure 1:
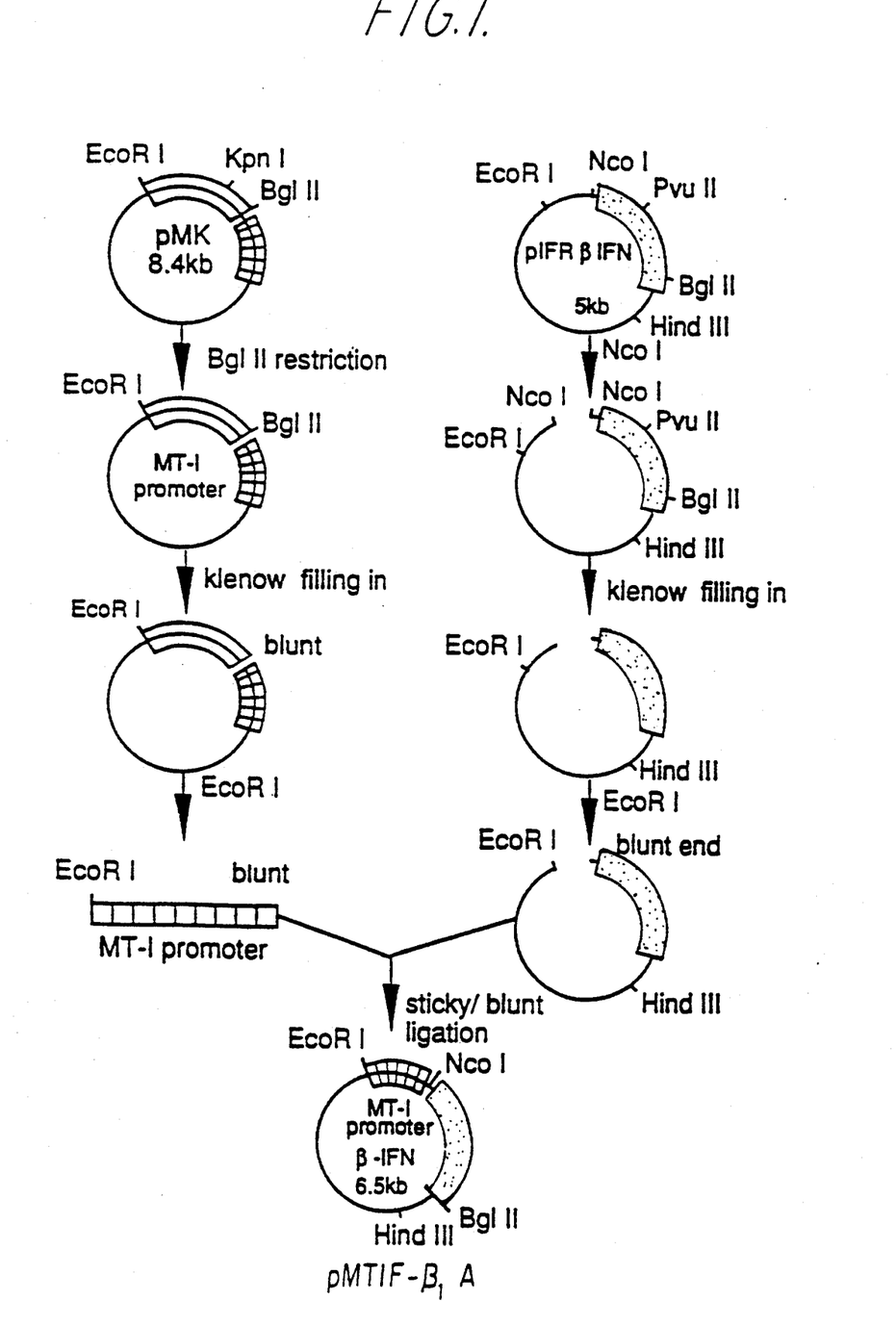
FIG. 1 shows the construction of pMTIF-beta$_1$A from pMK and pIFR-beta-IFN.
Figure 2:
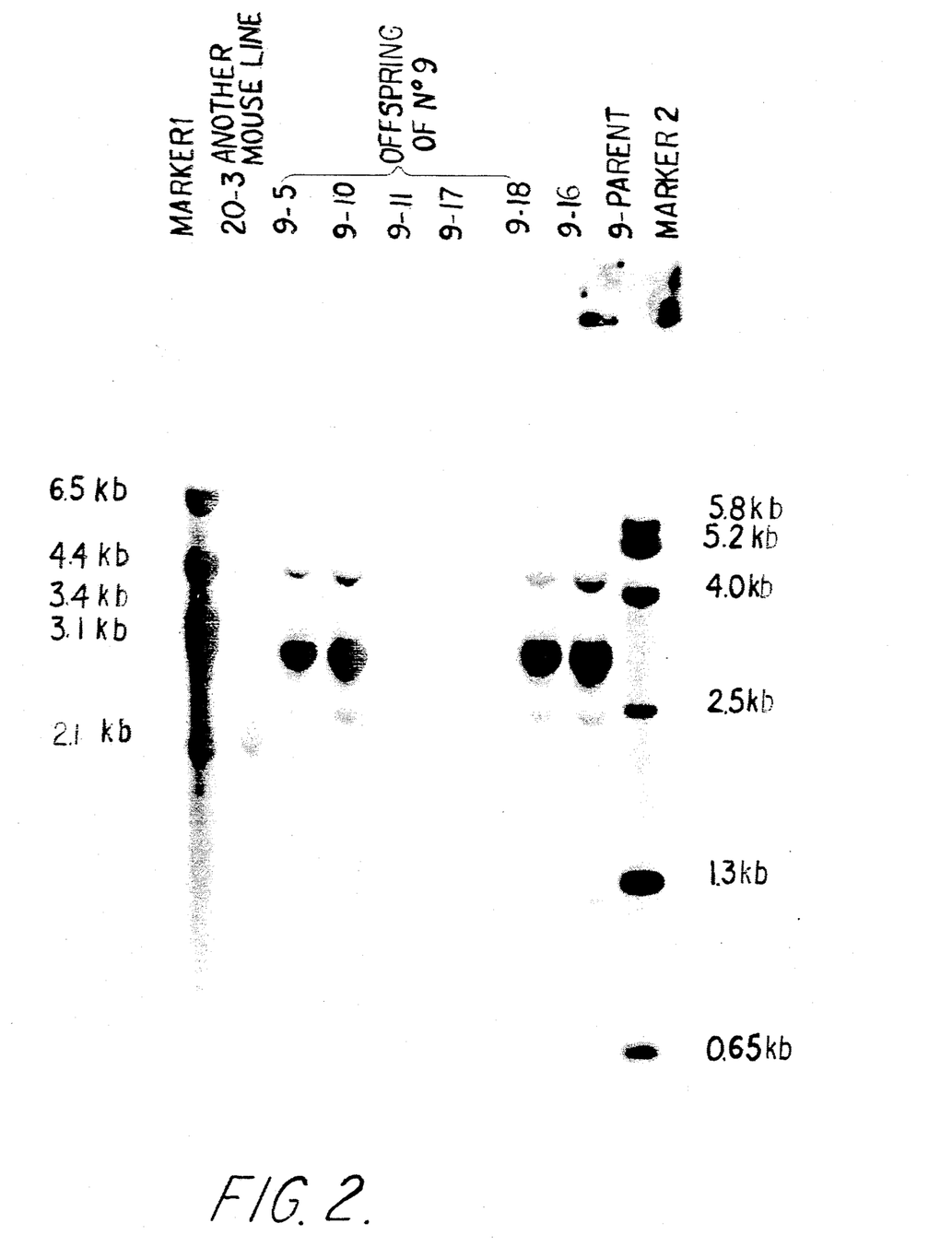
FIG. 2 is a southern blot of restriction fragments (double digestion with EcoR1 and PvuII) of DNA from the tails of transgenic mice. Each lane received 10 ug DNA, which was electrophoresed on a 0.8% agarose get at 50 v for 15 hrs., then transferred to a nitrocellulose filter. The 3.1 kb spots correspond to the EcoR1-PuvlI fragment of the human IFN beta gene.
Figure 3:
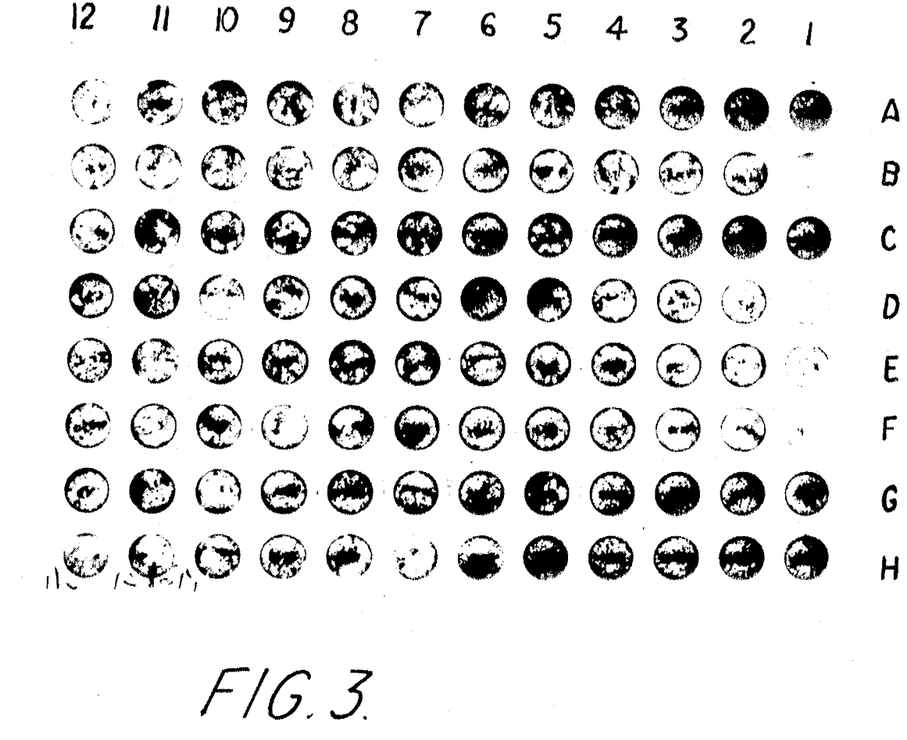

Microinjection of B-IFN Gene Into Mouse Zygotes and the Birth of Mice Containing the B-IFN Gene In Their Chromosome Linear DNA sequences (approx. 500 copies of a 3.1 kb EcoRI/Hind III fragment) from PMTIF-beta [A] and [B] were microinjected separately into the male pronucleus of fertilized mouse eggs. The eggs were transplanted into pseudopregnant female mice for gestation to term. At 3 to 4 weeks of age tissue from the tail of these mice was removed. Their DNA was analyzed for the presence of the integrated pMTIF-beta sequences within the mouse chromosomal DNA, as shown by hybridization to radioactively labeled pMTIF-beta probe DNA. Both "dot blot" and "Southern blot" hybridizations were performed (Molecular Cloning: A Laboratory Manual, T. Maniatis, E. F. Fritsch and J. Sambrook). For Southern blot hybridization, the chromosomal DNA was digested into fragments using restriction endonuclease which will cut the pMTIF-beta sequences into known lengths, both enzymes which cut twice within the pMTIF-beta sequences to demonstrate the authenticity of the added gene and once within the pMTIF-beta sequences and again within the adjoining chromosomal sequences to demonstrate integration. The 3.1 kb fragments which hybridize to probe DNA show the authenticity of the MTIF-beta sequences and the larger "junction" fragments demonstrate that the MTIF-beta sequences are integrated into the mouse chromosomes (see FIG. 1). Quantitation of the dot blot and Southern blot hybridizations indicate that mice having from 2 to 400 integrated copies of MTINF-beta were produced. Four transgenic mice with the pMTIF-beta [A] sequences in their chromosomal DNA out of 140 mice produced were found. Two transgenic pMTIF-beta [B] mice were produced out of 40 animals produced. These animals were mated and offspring produced. For all except one animal the integrated gene was transferred in a Mendelian fashion. One mosaic animal was identified which produce offspring which showed Mendelian genetics after the third generation.

EXAMPLE 3

Expression of Authentic Human Interferon Beta in Transgenic Mice Containing Integrated MTIF-beta A or B Sequence.

In order to demonstrate the capability of the MTIF-beta A and B fusion genes to express authentic human interferon in the mouse, secretions from mouse cells transfected with these sequences and serum from transgenic mice containing these sequences in their chromosomal composition were assayed for specific protection provided to human cells against viral infection using established standard human interferon assays.

Both pMTIF-betaA and pMTIF-betaB were used for a transient expression assay. The cell used was mouse L cell (in which MT-I promoter worked better than other cell lines considered, such as mouse 3T3 cells). When L cells are about 80% confluent, they are washed twice in DMEM minus serum (to get rid of nuclease activity), and 1.0 ug/ml of DNA (pMTIF-betaA OR betaB) and 0.2 mg/ml DEASE-dextran in DEAE minus medium are added to about 500,000 cells/ml. The mixture is incubated for one hour, then the DNA solution is removed and 10% DMSO in HEPES buffered saline is added to the cells for 90 seconds at room temperature. Next, the cells are washed first with PBS and then with growth medium (DMEM supplemented with 10% calf serum and gentamicin). Finally, growth medium is added to the cells and the cells are incubated at 37° C. for five days. Medium is changed every 24 hours up to the fifth day. Then the medium is used for cytopathic effect (CPE) assay and plaque reduction assay (PR). Familletti, et al., Methods. Enzymol., 78:387-94 (1981). The principle of the two assays are the same if there is human interferon in the media, the human cells incubated with the medium should be resistant to viral infection. The differences between the two assays are that in the plaque reduction assay, the exact number of plaques formed by viral infection can be counted but much more sample has to be used. For CPE assay, 96-well microtiter plate is used so that much smaller sample can be applied and serial dilutions can be easily carried out. However, in CPE assay, the number of the plaques cannot be counted and 50% killing (or protection) is arbitrarily assigned (very well trained eyes are needed for making this assignment). Thus, the viral plaque reduction assay was used for quantification and the CPE assay was used for both qualitative and quantitative purposes.

For performing the plaque reduction assay, small petri dish plates are used (with grids). First, human WISH cells are grown to confluency on the plates, then the media are removed, and plates are washed with PBS. The cells are subsequently incubated with media collected from the transient expression assay at different dilutions for at least 6 hours (usually it is overnight). Then the media is removed again, the cells are washed with PBS and then incubated with 50 PFU of vesicular stomatitis virus (VSV) for 30 minutes at 37° C. followed by pouring methycellulose-medium (serves as soft agar) on top of the cells. Next, the plates are incubated at 37° C. for 48 hours. Then the incubated plates are stained with methylene blue and the plaques are counted.

The major conclusion which were drawn from these PR assays were: a. media collected from transiently transfected cell culture showed anti-viral activities. They could protect human WISH cells from VSV infection whereas non-transfected cell media could not; more significantly, the media from pMTIF-betaB transfected cell cultures showed higher antiviral activity than that from pMITF-betaA transfected cell cultures, which indicated that mRNA transcribed from pMTIF-betaB is a more efficient transcript than mRNA from pMTIF-betaA. In other words, mRNA of pMTIF-betaB, in which the additional AUG (ATG in DNA) had been deleted, could be more efficiently translated into h-IFN-beta protein. The significance of this PR assay is that it showed that the construction of pMTIF-betaA and B is correct, that the plasmids could be expressed by mouse L cells, that the h-IFN-beta protein could be secreted from the cell. So, in theory, if these plasmids (or the MT-IFN fragments of these plasmids) are microinjected into mouse eggs and transgenic mice are generated, h-IFN-beta gene should also be expressible.

The 96-well microtiter CPE assay uses the same principle as the PR assay, and showed parallel results. First, 100 ul medium (DMEM plus 15% calf serum) was added to each well except for "#1" wells (first whole column). Then samples and medium were added to the #1 wells so each well contained 200 ul total. After completely mixing the samples in the #1 wells with medium, transfer 100 ul solution from each first well to the second well (that is, to make a 2× dilution), and then transfer to the third well, and so forth, until the last well is reached. Then add to each well 100 ul of human WISH cells (3×104 cells/100 ul) and incubate the cell-sample mixtures 6 hours to overnight. After incubation, add 50 ul VSV (3×103 PFU/50 ul) to challenge the cells in each well (except cell control wells), and incubate for 48 hours before staining. Next, stain with crystal violet and wash excess crystal violet stain away. Compare sample wells with IFN standards and controls of cells and cell-virus to determine protection and killing. The concentration of h-IFN-beta in the samples is determined on the basis that one unit of interferon is defined as the amount of interferon in a sample (at a certain dilution) which can give 50% protection to WISH cells against killing by VSV. In other words, the concentration of h-IFN-beta in the original sample is the reciprocal of the dilutions of a sample which showed 50% protection. CPE assays showed consistent results with PR, i.e., media from cell transfected with pMTIF-B had consistently higher activity than media from cells transfected with pMTIF-A.

Since the PR and CPE assays clearly showed interferon expression from cells transfected with MTIF-beta A and B demonstrating the functionally of these fusion genes to produce interferon in the mouse system, analyses were carried out on serum from transgenic mice containing MTIF-beta A and B to determine if these mice were producing interferon and specifically human interferon. The CPE assay was used to analyze the MTIF-beta mouse serum. The transgenic mice with the MTIF-beta A gene expressed 50 units of interferon per ml of serum, while the MTIF-beta B transgenic mice showed a level of interferon 3-5 fold higher. This difference in expression level is attributed to the greater efficiency of translation of the MTIF-beta RNA message in the MTIF-beta B mice resulting from the removal of the competing spurious ATG codon.

In order to confirm that the anti-viral activity of the sera of transgenic mice is due to the presence of human beta interferons, an antigen-antibody neutralization CPE assay was carried out. The difference between this assay and the standard CPE assay is simply to divide each mouse serum sample into two, one half of the sample was added to the first column well as before; the other half was mixed with horse anti-human beta interferon antibody and then was applied to another first column well. The serial dilutions were carried out after the sample was incubated with the antibody for 30 minutes or an hour. The co-incubation with cells, VSV challenging, staining are just the same as in common CPE assay. The result demonstrated that serum from transgenic mice could protect cells from viral infection whereas serum (same serum) preincubated with the antibody could not. This is a clear indication that the antiviral activity of the mouse serum on human cells was from human beta interferon. At the same time, negative serum control and antibody themselves could not protect the cells, which suggests that this antiviral activity is, and only is, from human beta interferon expressed in transgenic mice.

EXAMPLE 4

Viral Resistance of Transgenic Mice

Figure 4A:
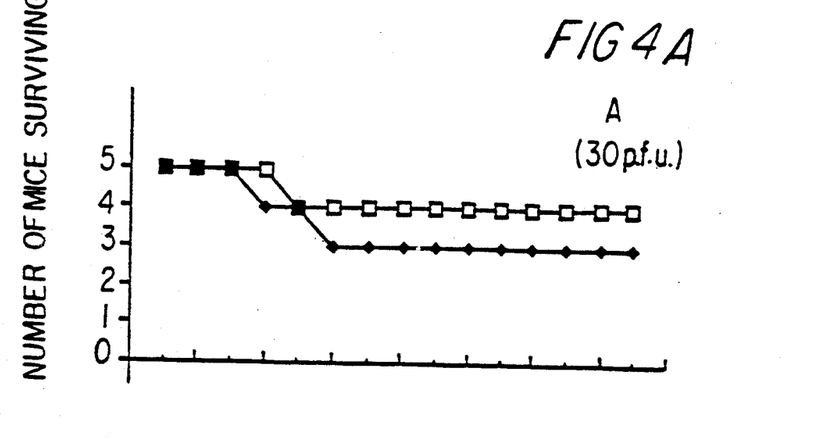
FIG. 4 shows the antiviral effect of human beta interferon in transgenic mice challenged with pseudorabies virus at three different levels of exposure (A, 30 p.f.u.; B, 60 p.f.u.; and c, 86 p.f.u.) In panels A and B, it is seen that the "A gene" appears to impart some resistance to the virus, which is more apparent in panel B. In panel C, we see the relative effects of the A and B gene.
Figure 4B:
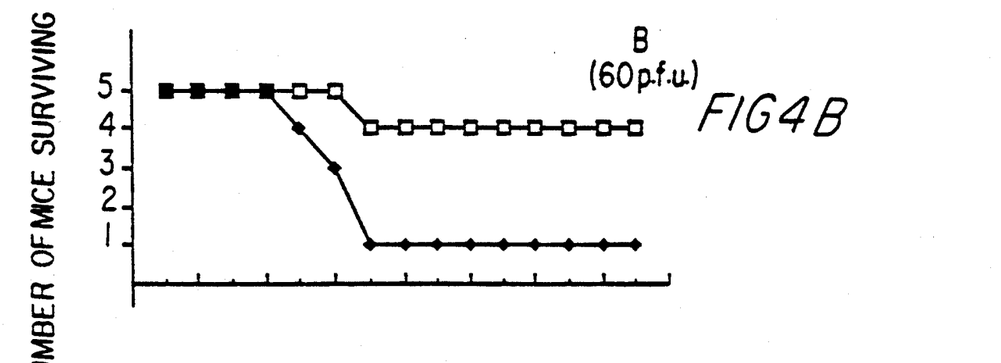
Figure 4C:
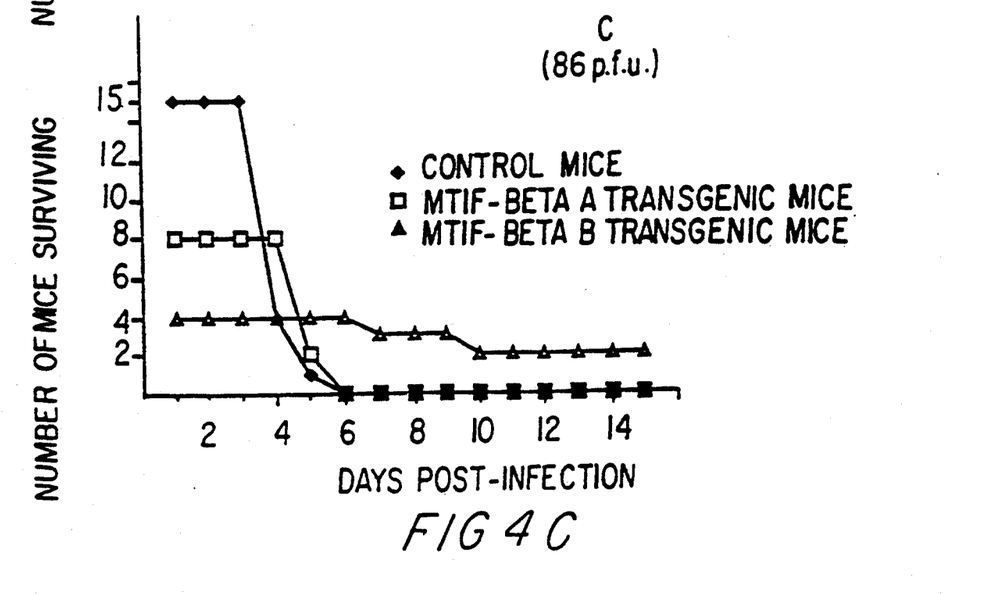

Transgenic mice containing the MTIF-beta A gene and mice containing the MTIF-beta A gene were produced as described in Example 2 and characterized as in Example 3. To evaluate the viral resistance of these mice, groups of mice were exposed to several concentrations of pseudorabies (RPV) (Rice strain 2-10-86), a virus lethal to mice, by footpad injection. Mortality was then compared with similarly inoculated controls. The results of this virus resistance assay are presented in FIG. 4. When mice were inoculated with increasing doses (p.f.u.) of the pseudorabies virus transgenic mice expressing human interferon beta consistently showed decreased mortality. At 30 p.f.u., 2 of 5 control mice died (40%) while only 1 of 5 MTIF-A transgenic mice died (20%). At 60 p.f.u. 4 of 5 control mice died (80%) while only 1 of 5 MTIF-Beta A transgenic mice died (20%). At 86 p.f.u. 15 of 15 control mice died (100%) while only 2 of 4 MTIF-beta B transgenic mice died (50%) and the human interferon gene-bearing transgenic mice died considerably later than did the control animals. When MTIF-beta A transgenic mice were challenged with the same dose of pseudorabies virus (86 p.f.u.) all of these mice died, but they died much later than did the control mice. The increased resistance shown by the MTIF-beta B mice is attributed to the 3-5 fold higher level of human interferon present within these animals. The mice used as controls were the same isogeneic F1 strain of mice as the transgenic mice, differing only in the presence of MTIF-beta DNA sequences in their chromosomal composition. These results are consistent with a finding that human interferon-expressing mice are virus resistant.

EXAMPLE 5

Proposed Protocol For the Production of Swine With Human Beta Interferon Gene

Swine containing the human interferon beta gene are constructed by microinjecting the MTIF-beta fusion gene into the one cell fertilized egg of the pig, transferring the developing embryo into a recipient female pig which ovulated at approximately the same time as the sow used to donate the fertilized eggs, and allowing the development of these eggs to term. When the pigs resulting from the microinjected eggs are born tissue samples are taken and analyzed for the presence of the MTIF-beta gene by hybridization analysis as described in Example 2 for the mouse. Pigs containing the MTIF-beta gene are then analyzed for expression of human beta interferon using the assays described in Example 3. Pigs expressing human beta interferon are then challenged with a virus, such as pseudorabies virus, to determine their resistance to viral infection.

We claim:

1. A transgenic mouse whose somatic and germ cells contain and express a gene coding for human beta interferon at a level sufficient to provide antiviral activity in said mouse, said gene having been introduced into said mouse or an ancestor of said mouse at an embryonic stage, and wherein said gene is operably linked to an at least partially constitutive non-interferon promoter.

2. The mouse of claim 1, said mouse being fertile and capable of transmitting said gene to its offspring.

3. The mouse of claim 1 wherein said gene has been introduced into an ancestor of said mouse at an embryonic stage by microinjection.

4. The mouse of claim 1 wherein said gene has been introduced into said mouse at an embryonic stage by microinjection.

5. The mouse of claim 1 wherein said at least partially constitutive non-interferon promoter is the metallothionein promoter.

6. A method of producing a mouse of claim 1 which comprises:

(a) providing a human beta interferon gene operably linked to an at least partially constitutive non-interferon promoter functional in a mouse, (b) introducing said gene into a mouse embryo, (c) transplanting said embryo into a pseudopregnant mouse, and (d) allowing said embryo to develop to term.

7. The method of claim 5 wherein said introducing is by microinjection.

8. The method of claim 5 wherein said at least partially constitutive non-interferon promoter is the metallothionein promoter.

* * * * *